US010888650B2

(12) United States Patent
Thiebaud et al.

(10) Patent No.: US 10,888,650 B2
(45) Date of Patent: Jan. 12, 2021

(54) TESTING OF A MEDICAL FLUID TREATMENT SYSTEM

(71) Applicant: Debiotech S.A., Lausanne (CH)

(72) Inventors: Pierre Thiebaud, Lausanne (CH);
Frédéric Neftel, Lausanne (CH)

(73) Assignee: Debiotech S.A., Lausanne (CH)

( * ) Notice: Subject to any disclaimer, the term of this patent is extended or adjusted under 35 U.S.C. 154(b) by 420 days.

(21) Appl. No.: 15/574,163

(22) PCT Filed: Jun. 3, 2016

(86) PCT No.: PCT/IB2016/053270
§ 371 (c)(1),
(2) Date: Nov. 15, 2017

(87) PCT Pub. No.: WO2016/193941
PCT Pub. Date: Dec. 8, 2016

(65) Prior Publication Data
US 2019/0209766 A1    Jul. 11, 2019

(30) Foreign Application Priority Data

Jun. 5, 2015   (EP) ..................................... 15170810

(51) Int. Cl.
*A61M 1/36*   (2006.01)
*A61M 1/28*   (2006.01)
(Continued)

(52) U.S. Cl.
CPC .......... *A61M 1/367* (2013.01); *A61M 1/1613* (2014.02); *A61M 1/1617* (2014.02); *A61M 1/1684* (2014.02); *A61M 1/28* (2013.01); *A61M 1/14* (2013.01); *A61M 2205/12* (2013.01); *A61M 2205/15* (2013.01); *A61M 2205/3331* (2013.01); *A61M 2205/50* (2013.01); *A61M 2205/70* (2013.01)

(58) Field of Classification Search
CPC .... A61M 1/14; A61M 1/1613; A61M 1/1617; A61M 1/1684; A61M 1/28; A61M 1/367; A61M 2205/12; A61M 2205/15; A61M 2205/3331; A61M 2205/50; A61M 2205/70

See application file for complete search history.

(56) References Cited

U.S. PATENT DOCUMENTS

2015/0198501 A1*   7/2015   Rule .................. A61B 5/15087
                                                        73/40.5 R
2017/0368248 A1   12/2017   Neftel et al.

FOREIGN PATENT DOCUMENTS

EP        0407737 A1    1/1991
EP        1648536 B1    4/2006
(Continued)

OTHER PUBLICATIONS

Japanese first Office Action, dated Mar. 11, 2020 for Application N° JP2017-561918.

(Continued)

*Primary Examiner* — Quynh-Nhu H. Vu
(74) *Attorney, Agent, or Firm* — Andre Roland S.A.; Nikolaus Schibli (57) ABSTRACT

The present invention relates to medical fluid treatments, such as the treatment of renal failure. More specifically, the present invention relates to the testing of such systems.

11 Claims, 4 Drawing Sheets

(51) Int. Cl.
*A61M 1/16* (2006.01)
*A61M 1/14* (2006.01)

(56) References Cited

FOREIGN PATENT DOCUMENTS

| | | | |
|---|---|---|---|
| EP | 1897605 A1 | 3/2008 | |
| EP | 1961566 B1 | 10/2008 | |
| JP | 03-057458 A | 3/1991 | |
| WO | WO01/12991 * | 3/2000 | ............. G01M 3/28 |
| WO | WO0012991 A1 | 3/2000 | |
| WO | WO2014020501 A1 | 2/2014 | |

OTHER PUBLICATIONS

International Search Report for PCT/IB2016/053270, dated Dec. 2, 2016.
Written Opinion of the International Searching Authority for PCT/IB2016/053270, dated Dec. 2, 2016.

* cited by examiner

TESTING OF A MEDICAL FLUID TREATMENT SYSTEM

CROSS REFERENCE TO RELATED APPLICATIONS

The present application is a United States national stage application of International Patent Application PCT/IB2016/053270 filed on Jun. 3, 2016 designating the United States, and claims foreign priority to European patent application EP 15170810.4 filed on Jun. 5, 2015, the contents of both documents being herewith incorporated by reference in their entirety.

FIELD OF INVENTION

The present invention relates to medical treatment systems for example adapted for providing a dialysis treatment. More specifically, the present invention relates to tests of systems, such as integrity tests or functional tests.

STATE OF THE ART

Dialysis systems are used for treating patients with inadequate kidney function. Dialysis systems typically include, among other things, a dialysate circuit comprising a pump. As described in the European Patent EP 1 648 536 B1 which is incorporated by reference to the present document, said system may comprise a disposable cassette in which is arranged a fluid pathway of the dialysate circuit. As described in the European Patent EP 1 981 566 B1 and the International Patent Application WO2014/020501 A1 which are incorporated by reference to the present document, said disposable cassette may comprise dedicated area designed to cooperate (operationally coupled) with a sensor (such as for example a pressure sensor), pumping mechanism and/or valve actuator.

Preferentially, the dialysis system comprises a disposable cassette and a reusable machine. The cassette is used only one time while the machine may be reused with several cassettes over time. Usually, the machine comprises expensive elements such as: actuator(s), sensor(s) or pumping mechanism(s). Said elements are designed in such a way as to cooperate with dedicated areas of the cassette. A dedicated area may comprise a flexible membrane adapted to be operationally coupled with a pressure sensor so as to allow a pressure communication between a fluid which flows through the cassette and the pressure sensor.

It is common in dialysis systems to perform some tests that attempt to verify several features of the system, such as the integrity of the fluid pathway of the disposable cassette, the functioning of the valves and/or the pump. These tests are always performed before starting the treatment and the vast majority of these tests are performed to check that no leakage (of the fluid which flows into the fluid pathway of the cassette) occurs. But other problems may occur and the prior art systems are not adapted or designed to find these other failures.

For example, in operating configuration, the cassette is coupled to the machine and each element has to be correctly interfaced with its dedicated area. But, the coupling between the cassette and the machine may sometimes fail. In this case, some elements cannot be fully operated with the risk of, for example, compromising the efficiency or the safety of the treatment. Thus, said defects have to be detected so as to ensure the safety of the patient.

Furthermore, some elements may wear over time, for example the sensors. Thus, it should be noticed that the sensor should also be tested in such a way as to check the smooth operating of the sensor.

The present invention overcomes the drawbacks of the prior art by performing other tests so as to increase the patient security and/or to monitor the operating elements of the system.

A discussion of the features and advantages of the present invention is deferred to the following description, which proceeds with reference to the accompanying drawings.

Figure 1A:
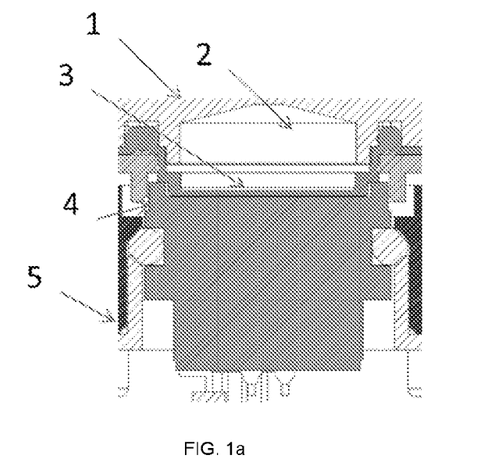
FIGS. 1a and 1b show a pressure sensor and a part of a disposable cassette
Figure 1B:
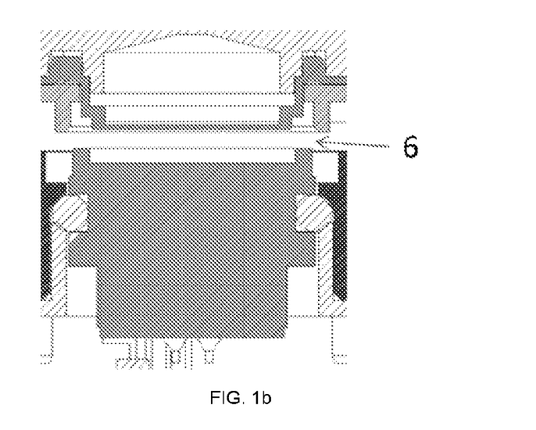

The FIGS. 1a and 1b show a pressure sensor and a part of a disposable cassette (in particular, an area which is dedicated to the pressure measurement). In the FIG. 1a, the sensor and the dedicated area are correctly interfaced while in the FIG. 1b, the sensor and the dedicated area are not correctly interfaced. The gap between both elements is overly emphasized as to better visualize the difference between the two situations. Nevertheless, when the sensor is correctly coupled with the dedicated area, a small volume of a fluid (for example air) is potentially trapped between the sensor and the dedicated area of the cassette. The coupling has to be tight so that the sensor measures pressures.

The present description makes a distinction between the fluid which flows through the fluid pathway of the cassette and the fluid trapped as described above. The fluid which flows through the fluid pathway may be blood, water, drug or dialysate and the fluid which is trapped between the sensor and the dedicated area of the cassette may be a gas or a liquid but, preferentially, it is different from the fluid which flows through the fluid pathway of the cassette. Nevertheless, before the priming of the fluid pathway (or after the treatment), the fluid which is into the fluid pathway (of the cassette) may be air. Thus, if the test is performed before the priming or after the treatment, the fluid which flows—during the test—through the fluid pathway may be substantially similar for example: air.

When the fluid (which flows into the cassette) is subjected to a greater pressure than the atmospheric pressure (in other terms, when the fluid pressure is positive), the membrane of the dedicated area may come into contact with (or may move or may be deformed towards) the sensor. Thus, the membrane and/or the fluid trapped push a surface of the sensor and the sensor measures a pressure. But, when the fluid (which flows into the cassette) is subjected to a lower pressure than the atmospheric pressure (in other terms, when the fluid pressure is negative), a good or sufficient coupling between the dedicated area and the sensor is necessary for measuring such negative pressure. Indeed, the membrane of the dedicated area may move or may be deformed in a direction opposite of the sensor and thus the depression of the trapped fluid allows measuring a negative pressure (in one embodiment, the depression of the fluid trapped pulls a surface of the sensor so as to measure a negative pressure). Thus, no leakage shall occur between both elements. In other terms, the fluid pressure of the fluid (which flows through or in the cassette) is transmitted to a surface of the sensor (or to the sensor) via the membrane and/or the fluid trapped (between the membrane of the cassette and the surface of the sensor).

Figure 3:
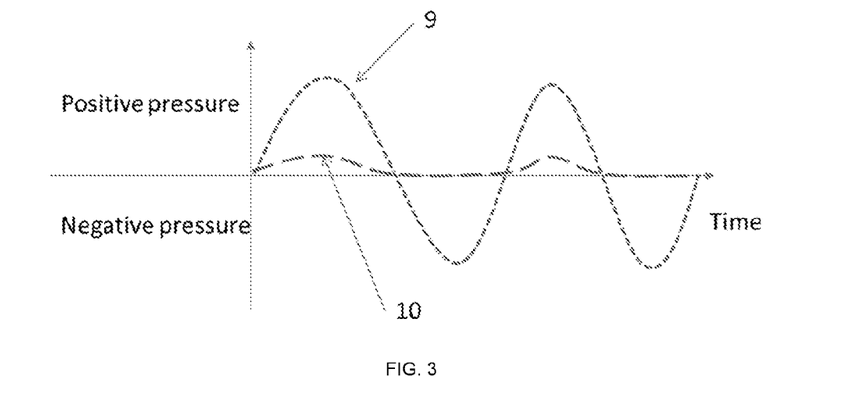
FIG. 3 shows the data (7) measured by a pressure sensor.

In the case where a leakage of the trapped fluid occurs, if the pressure of the fluid (which flows through the fluid pathway of the cassette) is positive, the pressure sensor may still be able to measure a positive pressure: for example the membrane of the cassette will come into contact with the surface of the sensor and pressure can be measured. But if the pressure of the fluid (which flows through the fluid pathway of the cassette) is negative, the surface of the sensor will not be influenced by the deformation of the membrane of the cassette and the pressure sensor may potentially measure the atmospheric pressure. In other terms, the negative pressure cannot be measured due to the leakage of the fluid trapped. For example, the curve (9) of the FIG. 3 represents the real pressure of the fluid flowing through the fluid pathway of the cassette but the curve (10) of the FIG. 3 shows data measured by a pressure sensor of the machine when a leakage of the fluid trapped occurs. Both curves (9, 10) should be the same but the curve (10) records a low underestimated positive pressure (caused by the imperfect contact of the membrane against the sensor) and no negative pressures is detected.

When the leakage is limited or if the sensor is not totally defective, the data measured may record positive and negative pressures. Nevertheless, the data measured may be substantially different from the real pressure and it may be hazardous for the patient or the treatment. Thus, in this case, the system cannot detect the failure.

Usually, one solution is to include two redundant sensors in the system so as to compare the data of both sensors. Thus the primary sensor is compared to the second sensor so as to detect a failure of sensor(s). This first solution may detect a failure of one sensor, in particular when one of said sensors measures a pressure which is close to the atmospheric pressure or when one of said sensors is totally defective. But when the coupling (for example of both sensors) is not perfectly working, both sensors may record the same data and the system cannot detect any defect.

Furthermore, due to the wear of the system, the coupling or the sensor may be gradually deteriorated without the system even noticing it. Indeed, even if the sensor records negative and positive pressures, the system may get defective.

Thus, preferably, the machine and/or the cassette should be changed before this failure affects patient health.

GENERAL DESCRIPTION OF THE INVENTION

The aim of the invention is to detect an operating failure due to a bad coupling or a defective element (such as a sensor) as quickly as possible so as to limit the impact to the patient's health. The present document describes distinct methods to detect such failure which may be used alone or together:
   A test in which a pump generates a pressure;
   The monitoring of the pulsation amplitudes which are generated by the pump during, for example, the treatment;
   The drop and/or the increase of the pressure generated by the fluid which flows through the fluid pathway, for example during the treatment;
   A final test in which a pump generates a pressure.

A first aspect of the invention is a method for detecting a failure in a system adapted to provide a medical treatment to a patient. This system may comprise a fluid pathway (removably and/or fluidically) connected to the patient and be adapted to infuse or to remove a fluid to or from the patient via the fluid pathway.

In one embodiment, the method may comprise the following successive steps:
   After the medical treatment is completed, blocking the fluidic communication between the patient and the fluid pathway;
   Performing a test so as to detect a failure, wherein the test consists in checking a feature of the fluid pathway or an element interacting with the fluid pathway.

As used herein, "blocking" refers to an action which allows preventing or avoiding the fluid communication by closing or by cutting or by disconnecting the fluid pathway to the patient.

In one embodiment, the system comprise a pump adapted to move the fluid through the fluid pathway and a sensor adapted to measure a feature associated to the fluid pumped, the method may comprise the following successive steps:
   Actuating the pump;
   Monitoring the pressure measured by a first sensor;
   Sending at least one measured pressure to the processor;
   Determining whether a failure is present by processing the measured pressure.

In one embodiment, the system comprises at least one occlusion element adapted to block or close the fluid pathway, the method may comprise the following successive steps:
   Closing the fluid pathway via the occlusion element in such a manner as to define a closed pathway between the pump and the occlusion element,
   Actuating the pump so as to generated a positive or negative pressure into the closed pathway;
   Monitoring the pressure measured by a first sensor which is in pressure communication with the fluid being in the closed pathway;
   Sending at least one measured pressure to the processor;
   Determining whether a failure is present by processing the measured pressure.

A second aspect of the invention is a method for automatically testing the coupling between two distinct elements, said method may be performed by a medical system which may comprise a pump, a sensor, an electronic processor and a cassette. The cassette may comprise a dedicated area and a fluid pathway. The dedicated area may be adapted to be removably coupled to the sensor and to be in interaction with the sensor in such a manner as to monitor the pressure in the fluid pathway. The pump id adapted to convey a fluid through the fluid pathway. The method is performed to monitor the coupling between the sensor and the dedicated area; the method may comprise the steps of:
   Actuating the pump
   Monitoring the pressure measured by the sensor
   Sending the measured pressure to the processor
   Processing the data by the processor so as to check the coupling of said distinct elements.

The fluid pathway may comprise at least one valve which is controlled by the processor. The method may comprise the following steps closing at least one valve so as to define a temporarily closed pathway within the fluid pathway.

A third aspect of the invention is a method for monitoring the smooth operating of a medical system which may comprise a pump, a sensor, an electronic processor and a cassette. The cassette may comprise a dedicated area and a fluid pathway in which a fluid is conveyed by the pump. The dedicated area is adapted to be removable coupled to the sensor and in fluid or pressure communication with the fluid pathway and the sensor, the method may comprise the steps of:
   Actuating the pump
   Measuring the pulsation amplitudes of the fluid pressure generated by the pump
   Sending the measured data to the processor
   Processing the measured data by the processor A fourth aspect of the invention is a method for monitoring the smooth operating of a medical system adapted to perform a medical treatment to a patient. The medical system may comprise a pump, a sensor, an electronic processor and a cassette. The cassette may comprise a dedicated area and a fluid pathway in which a fluid is conveyed by the pump. The dedicated area is adapted to be removable coupled to the sensor and in fluid or pressure communication with the fluid pathway and the sensor, the test method may comprise the steps of:

Actuating the pump
Measuring fluid pressure by the sensor
Sending to the processor
Processing the data by the processor In one embodiment, this method is performed after the medical treatment of the patient has been completed.

In one embodiment, the method may comprise the following steps:

Actuating the pump until a measured pressure by a first sensor reaches a threshold
Measuring a fluid pressure by a second sensor
Computing by the processor the difference of measured pressures by both sensors.

LIST OF FIGURES

The present invention will be better understood at the light of the following detailed description which contains non-limiting examples illustrated by the following figures.

LIST OF ELEMENTS

1 Cassette
2 Fluid pathway
3 Dedicated area
4 Sensor
5 Machine
6 Gap
7 Data of the measured pressure
8 Average of the measured pressure
9 Real pressure of the fluid flowing through the cassette
10 Data record by a defective sensor or when a leakage of the fluid trapped occurs
101 Patient
102 Machine
103 Machine
104 Bag of dialysate
105 Bag of waste fluid
106 Processor
107 Pump actuator
108 Sensor
109 Display device
110 Valve actuator
111 Other means
201 pump
202, 203 specific area
204, 205 sensor
206, 207 occlusion element
208 first end
209 second end
300 medical system
301 patient
302 supply bag
303 waste fluid bag
304, 305, 306, 311, 312 occlusion element
307 pump
308, 309, 310 sensor

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" is generally employed in its sense including "and/or" unless the content clearly dictates otherwise.

Figure 4:
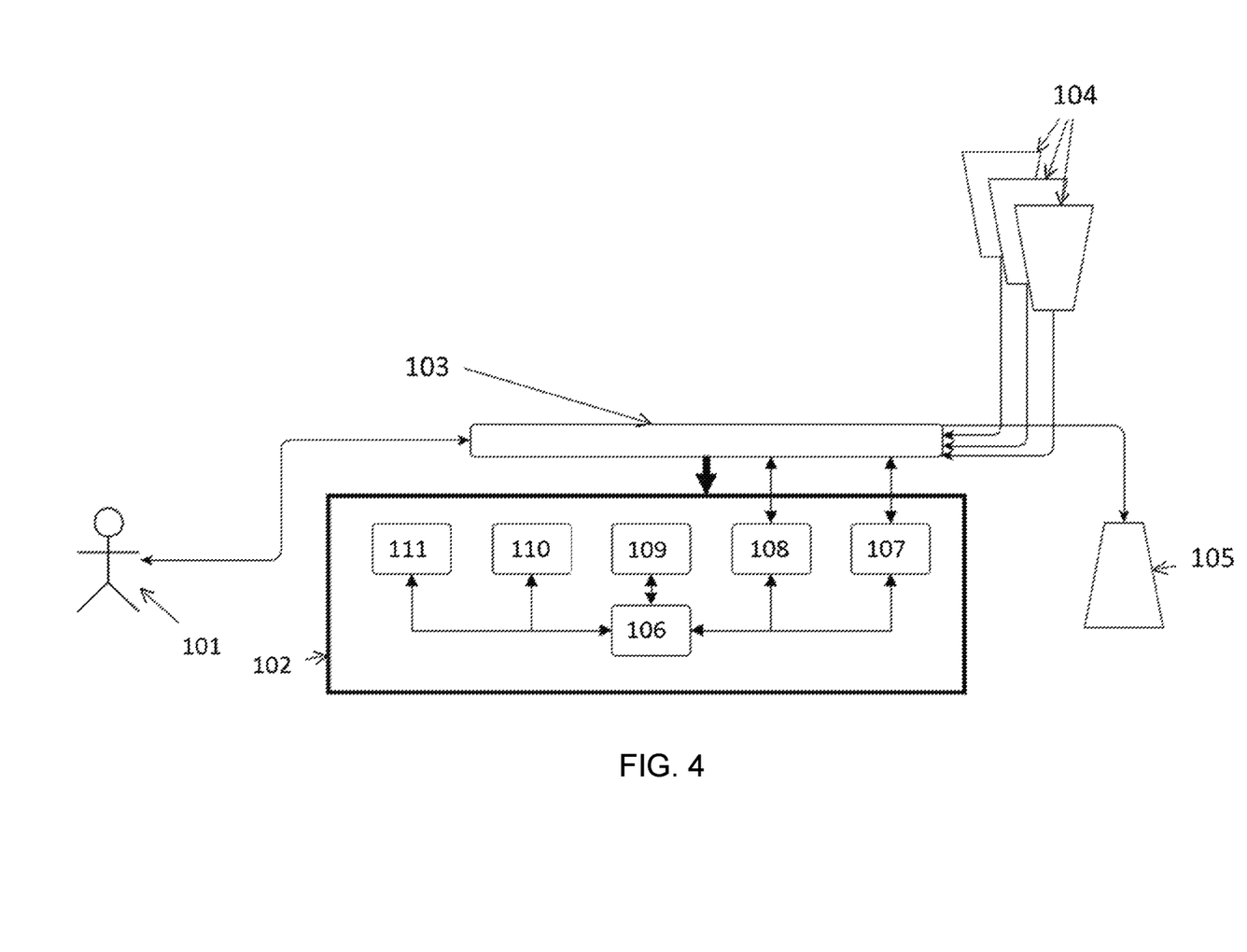
FIG. 4 shows an embodiment.

The FIG. 4 illustrates a dialysis treatment system which comprises a dialysate circuit, a pump and at least one bag for fresh or waste dialysate. The patient (for example, in case of peritoneal dialysis, the peritoneal cavity of the patient), the dialysate circuit, a part of the pump and/or the bag may be fluidly connected. The system may further comprise a pump actuator (107), at least one sensor (108), a display device (109) (which may be a touch screen) and other means (110, 111), for example input means (keypad, bouton, . . . ). All of these elements may be connected to, and/or used with and/or controlled by an electronic processor (106).

Preferentially, the system comprises a machine (102) (for example a cycler) which may comprise expensive and reusable elements and a cassette (103) which may comprise a part of the fluid pathway and occlusion means adapted to direct a fluid (for example dialysate) through the fluid pathway. The cassette may comprise at least one tube which extends from the cassette to bag and/or patient in a way as to make a fluid pathway in fluid communication with the peritoneal cavity of the patient and/or a supply bag (104) and/or a waste bag (105). The fluid may be directed thanks to the fluid pathway and the opening or the closing of the occlusion means). The machine (102) is adapted to be operationally coupled with the cassette (103) which may be a disposable element as described above.

The machine may comprise at least one sensor (108) (for example a pressure sensor) and a pump actuator (107) which actuates a pump designed to move a fluid through the fluid pathway of the cassette. The cassette (103) may comprise dedicated area(s) designed to cooperate with the sensor or pump actuator of the machine. The dedicated area is adapted to be in fluid or pressure communication with the fluid which flows through the fluid pathway. And, the dedicated area may be adapted to be in fluid or pressure communication with the sensor. The sensor may be adapted to measures a fluid pressure of the fluid which flows through the fluid pathway. The dedicated area may be made of a flexible membrane. In operating configuration, the dedicated area has to be correctly coupled to the sensor so as to measure correctly the pressure. In one embodiment, the machine may comprise at least one valve actuator (110) designed to cooperate with another dedicated area of the cassette (for example occlusion means or valve which closes the fluid pathway in the cassette) as to close or open a fluid pathway of said cassette. The system may comprise other occlusion means (for example clamp) which may be arranged on and/or adapted to close the fluid pathway of the system (for example on the tube which extends from the cassette to the patient or bag).

The pump may be activated in a way as to generate a positive or negative fluid pressure into the fluid pathway (in particular if a occlusion means closes a part of the fluid pathway). The fluid used during the test may be a dialysate solution or other (gas (air, . . . ), liquid, . . . ).

The FIG. 1a shows a dedicated area (3) of the cassette (1) which is correctly coupled to a sensor (4) of the machine (5), some fluid (for example air) may be trapped between the dedicated area (which may be a flexible membrane) and a surface of the sensor, in particular a surface which can measure a pressure. The FIG. 1b shows a dedicated area (3) which is not correctly coupled to the sensor (4), a gap (6) is between said area (3) and the sensor (4). In this last case, the fluid (air) cannot be trapped between the membrane and the sensor. In both figures, the cassette comprises a fluid pathway (2) which is in fluid and/or pressure communication with the dedicated area (3). Said dedicated area transmits the pressure (of the fluid which is into the fluid pathway (2)) to the sensor (4). As described above, the negative pressure can be measured by the sensor only if said elements are correctly coupled.

As described above, the system may comprise an occlusion element (so called occlusion means) allowing the closing of a part of the fluid pathway. Said occlusion element may be closed during at least a part of the test. Said occlusion element may be a valve of the cassette (as described above), a connector cap, clamp, . . . . Thanks to this occlusion element, during the test, the system may determine a part of the fluid pathway in which the test will be performed. For example, as shown by the FIG. 5, if the system tests the sensor (204, respectively 205) which is downstream (respectively upstream) of a pump (201), the system may close an occlusion element (206, respectively 207) which is located before (respectively after) the sensor (204, respectively 205). In other terms, the system may close the fluid pathway (208, 202, 203, 209) of the dialysate circuit so as to define a temporarily closed pathway (202, 203) within the fluid pathway, which extends from a valve (206) to a pump (201) (or from a pump (201) to a valve (207)). Preferentially, said temporarily closed pathway comprises at least one dedicated area (as described above) adapted to cooperate with a sensor (204, 205) which is used for the test.

Failure Detected by a Test Generating a Pressure by a Pump

In this test, the pump generates a pressure preferentially in a temporarily closed pathway (as described above). The system controls the pump and monitors the sensor during the test. The objective of such test is to detect that the pressure data reaches a pre-determined threshold. Thus, the pump is actuated by the system so as to generate a negative or positive pressure in the temporarily closed pathway which cooperates with the tested element (as the pressure sensor or the coupling). Said test may comprise other condition(s), for example, the threshold has to be reached before a predetermined time interval or a predetermined number of pump strokes or a predetermined volume of fluid pumped . . . . After the test, the system may stop the pump and may pass to another test or to the treatment. For example, if the system concludes to a failure or a success, the system passes to another test (for example so as to confirm the result or to check others elements) and/or records the data in a memory of the system and/or performs the treatment.

These other conditions of the test may be also used to limit the test duration or the fluid volume which is pumped during the test. Thus, the system may stop the test after a predetermined time or after a predetermined number of strokes or when a predetermined volume of fluid has been pumped.

Preferentially, if condition is not met (for example: the data of the measured pressure does not reach the predetermined threshold during a predetermined number of pump strokes), then the system may conclude to a failure.

During this test, the system may maintain a pressure into the temporarily closed pathway and monitor, over a certain time, the pressure measured by the tested sensor. If the data of the measured pressure goes beyond a predetermined range (e.g. decays faster than a given rate), the system may conclude to a failure.

Figure 5:
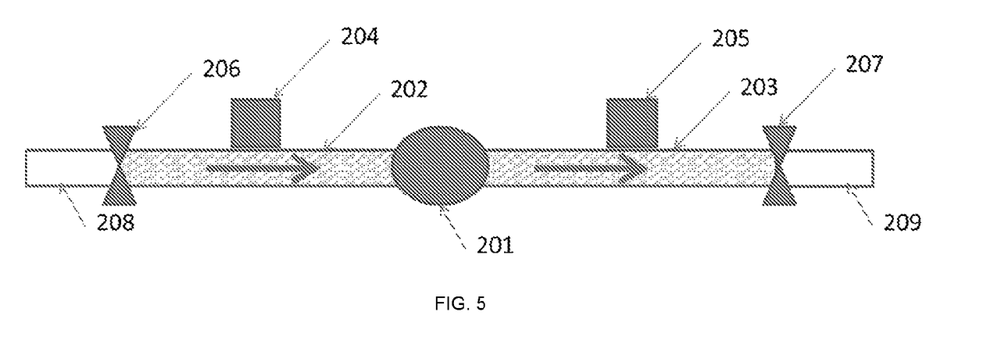
FIG. 5 illustrates a fluid pathway of an embodiment.

The test may comprise the following step:
Closing the fluid pathway with an occlusion element to define a temporarily and determined closed pathway (202, 203) within the fluid pathway;
Actuating the pump (201) to generate (successively) a predetermined positive and/or a negative pressures in said temporarily and determined closed pathway (202, 203);
Sending, to the processor, data of the pressure sensor (204, 205) which is in pressure communication with said temporarily and determined closed pathway (202, 203);
Analyzing by the processor the received pressure data from the pressure sensor.

Optionally, the system maintains the positive and/or the negative pressures during a predetermined duration and the system monitors the profile of the pressure data during said predetermined duration. To maintain the pressure, the system may stop the pump or actuate slowly the pump.

The pump may generate a positive pressure so as to detect a leakage of the fluid which flows into the fluid pathway. And the pump may generate a negative pressure so as to detect a leakage of the fluid trapped between the sensor and the membrane (the dedicated area which is adapted to cooperate with the sensor). Thus, a failure of coupling may be preferentially detected thanks to the negative pressure generated by the pump.

The pump (201) may be a peristaltic pump or a diaphragm pump. In this last case, the element (201) may comprise additional valves dedicated to the pump mechanism. As shown in the FIG. 5, in a normal actuation mode, the pump (201) moves the fluid from a first end (208) of the fluid pathway to a second end (209) of the fluid pathway and, in a reverse actuation mode, the pump (201) moves the fluid from the second end (209) of the fluid pathway to the first end (208) of the fluid pathway.

The test may check two distinct sensors (204, 205), a first sensor (204) which is located downstream of a pump (201) and a second sensor (205) which is located upstream of a pump (201). Four distinct tests may be successively performed (the order of the following step can be changed):

- Generating a positive pressure in the temporarily closed pathway (203) which is in pressure communication with the second sensor (205);
- Generating a positive pressure in the temporarily closed pathway (202) which is in pressure communication with the first sensor (204);
- Generating a negative pressure in the temporarily closed pathway (202) which is in pressure communication with the first sensor (204);
- Generating a negative pressure in the temporarily closed pathway (203) which is in pressure communication with the second sensor (205).

To generate a positive pressure in the first temporarily closed pathway (202), the pump may be actuated in the reverse actuating mode, the first valve (206) is closed and the second valve (207) is open. To generate a negative pressure in the first temporarily closed pathway (202), the pump may be actuated in the normal actuating mode, the first valve (206) is closed and the second valve (207) may be open. To generate a positive pressure in the second temporarily closed pathway (202), the pump may be actuated in the normal actuating mode, the first valve (206) is open and the second valve (207) is closed. To generate a negative pressure in the second temporarily closed pathway (202), the pump may be actuated in the reverse actuating mode, the first valve (206) may be open and the second valve (207) is closed.

The processor analyzes the received pressure data from the first and second sensors. If during the first test, the received pressure data from the first sensor reaches a predetermined threshold (for example during a predetermined number of pump strokes), then the process may conclude that no leakage of the fluid occurred in a part of fluid pathway downstream of the pump (201). If during the second test, the received pressure data from the first sensor reaches a predetermined threshold (for example during a predetermined number of pump strokes), then the process may conclude that the first sensor is correctly coupled to the cassette. If during the third test, the received pressure data datafrom the second sensor reaches a predetermined threshold (for example during a predetermined number of pump strokes), then the process may conclude that no leakage of the fluid occurred in a part of fluid pathway upstream of the pump (201). If during the fourth test, the received pressure data datafrom the second sensor reaches a predetermined threshold (for example during a predetermined number of pump strokes), then the process may conclude that the second sensor is correctly coupled to the cassette.

If any of those received pressure data cannot reach the predetermined threshold or maintain a value above such threshold over a certain time, then the system may indicate to the patient or caregiver (which may be located on other area) via a screen, e-mail or audio indication that the system cannot perform the treatment. If only few received pressure data cannot reach the predetermined threshold or maintain a value above such threshold over a certain time, then the system may indicate this information only to the caregiver and it may perform the treatment in a safety operating mode (as described in the European patent application number EP 14189455.0 which is incorporated by reference to the present document) in which the result of treatment is not optimal but better than no treatment, while the security for the patient is ensured via a modified treatment cycle.

This test or a similar test may be performed when the patient is no longer fluidly connected to the system (for example to the dialysate circuit of the system). Thus, the fluid pathway may comprise an element adapted to prevent the fluidic communication between the fluid pathway of the system (for example the cassette) and the patient (for example to the peritoneal cavity of the patient). For example, the system may comprise an occlusion element which closes the fluid pathway between the cassette and the patient (such as for example a valve, a clamp, . . . ). The system may also comprise a connector which allows the fluid communication between the system and the patient during the treatment. In this case, the patient can disconnect from the system before the test procedure. This connector may further comprise a cap which may be used to close this end of the fluid pathway during the test procedure. Before to start the test procedure, the system may check that the patient is no longer in fluid communication with the system. For example, the system may actuate the pump and monitor the pressure data.

The fluid circuit may comprise a flexible area (for example a tube, a membrane, a connector, a wall of the cassette, . . . ). Said flexible area may be deformed over time by the pressure generated by the pump. Thus, the system has to use a mathematical model which takes into account this deformation over time. Because, the fluid pressure may change over time due to the deformation of the flexible area. Thus, the system has to determine if the evolution of the pressure data is due to a leakage or the deformation of the flexible area (for example the flexible tube of the system).

The system may perform these tests over a short period of time and therefore the system doesn't have to take into account the thermal evolution which may cause over time a drift of the pressure.

Failure Detected by the Pulsation Amplitude

Figure 2:
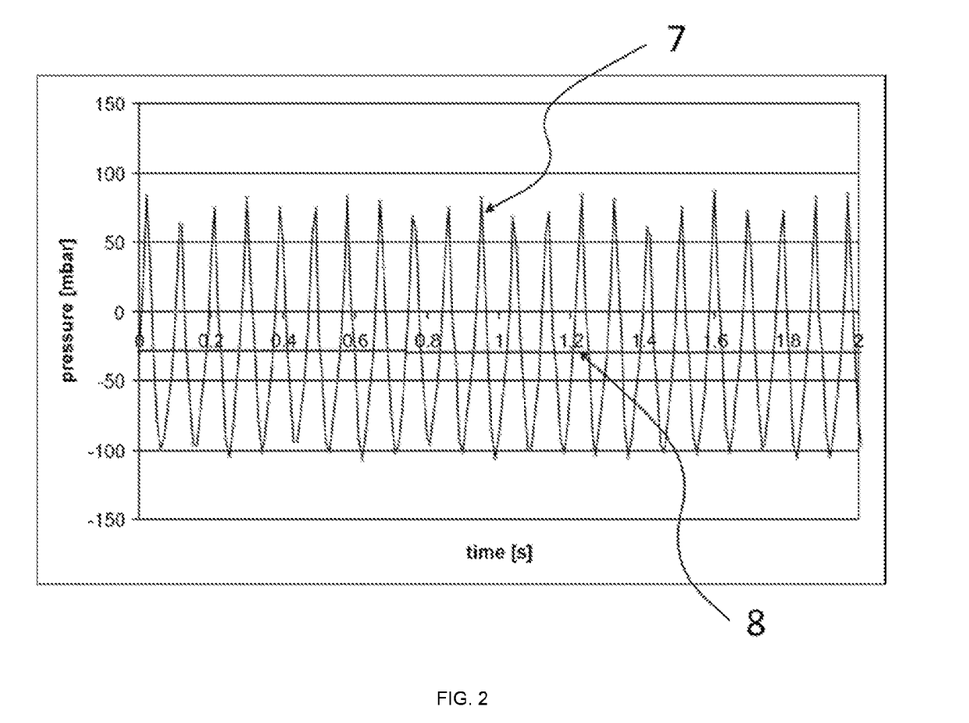
FIG. 2 shows the data (7) measured by a pressure sensor.

If the pump is a diaphragm pump or a peristaltic pump, both may generate pulsations (peaks of pressure) which shall be detected by a pressure sensor. The FIG. 2 shows the data (7) measured by a pressure sensor. Said data (7) draws a curve of the pulsations generated by a peristaltic pump. Said curve (7) comprises maximum pressure peak and minimum pressure peak. The curve (8) is the average of the data (7).

This test may be performed after a previous test, for example if the system does not detect any defect. It may be performed when the patient is fluidly connected to the fluid pathway (for example the dialysate circuit) before the treatment and/or during the treatment and/or after the treatment. During the test, unlike the test previously described, the system may not define a temporarily closed pathway within the fluid pathway.

When the sensor and the dedicated area are not correctly coupled (or if a sensor has a defect), the pressure data sent by the pressure sensor is not substantially equal to the "normal" profile of predetermined data. The "normal" profile of predetermined data is the profile of data which corresponds to the measured pressure pulsations when the system operates correctly. The processor may compare the received pressure data from the pressure sensor to predetermined data so as to detect a defect.

Preferentially, the test comprises the following steps:
Optionally, opening valves of a fluid pathway which extends from a supply of fluid to a receiver of fluid,
Actuating a pump,
Sending to the processor the pressure data measured by a pressure sensor which is in pressure communication with the fluid moved by the pump,
Analysing by a processor the received pressure data from the sensor.

The supply of fluid and the receiver of fluid may be a cavity of the patient (for example the peritoneal cavity) or a bag.

The processor may use a mathematical model to analyse the data, for example to compare the pressure data measure to a reference (range, threshold, computed data, . . . ).

During this test, the processor may monitor, for example, the minimum, maximum of a peak of pressure data and/or average values (8) of the pressure data. Thus, the processor may compare:
A minimum of the pressure data to a predetermined threshold or to a predetermined range, and/or
A maximum of the pressure data to a predetermined threshold or to a predetermined range, and/or
The average of the minimum of the pressure data to a predetermined threshold or to a predetermined range, and/or
The average of the maximum of the pressure data to a predetermined threshold or to a predetermined range, and/or
The difference between a minimum and a maximum of the pressure data to a predetermined threshold or to a predetermined range, and/or
The difference between the average of the minimum and the average of the maximum of the pressure data to a predetermined threshold or to a predetermined range.

For example, in case where the processor computes the difference between a top pressure data (a maximum of the pressure data) and the bottom pressure data (a minimum of the pressure data) during a predetermined duration, (in other terms the difference between the maximum and the minimum measured data) the difference has to be higher than 10 mbar, 20 mbar or 50 mbar so as to conclude to a smooth operating of the system.

If data monitored by the processor is not correct, the system may conclude to a defect. This defect may trigger an alarm to inform the patient or a caregiver or may be recorded to a memory of the system to be used after.

Said test may be performed at a specific time (before or during the treatment) or over time of the treatment.

Failure Detected by the Drop and/or the Increase of the Pressure Generated by the Fluid into the Fluid Pathway The pumping of the fluid generates some fluid frictions against the walls of the cassette. Said pressure caused by the friction depends on the flowrate of the fluid, the shape of the fluid pathway, and the features of the fluid and of the fluid pathway. This pressure may be computed for example using the formula Poiseuille-Hagen. This formula is valid in the case of a pressure generated by a laminar flow in a tube.

When a peristaltic pump is actuated in a normal actuating mode, a negative pressure is generated upstream the pump (201) and a positive pressure is generated downstream the pump (201). As described above, when the coupling is not correct, the system cannot measure the negative pressures while the positive pressure may be more easily measured.

Thus, it would be better to monitor the pressure in the fluid pathway located before the pump.

If a small leakage occurs between the sensor and the dedicated area, the measured pressure slowly derives. A threshold or a range may be determined and if the measured pressure reaches said parameters, during the treatment, the system has to act so as to ensure patient safety.

In the case of the peritoneal dialysis treatment, the system performs several cycles of fill, dwell and drain phases. During the fill and the drain phases, the pump is actuated so as to move the dialysate from the supply by to the peritoneal cavity of the patient and from the peritoneal cavity of the patient to a waste fluid bag.

During the test, the system receives the pressure data from the pressure sensor before starting the actuating of the pump. Said pressure data is recorded in a memory of the system and is compared to the pressure data when the pump is actuated. The description of this test is fully described into the European patent application EP 14189455.0 which is integrally integrated into the present document.

The test comprises the following steps:
Receiving a pressure data from a pressure sensor when the pump is not actuated
Actuating the pump so as to move a fluid through a fluid pathway at a specific flow rate
Receiving the pressure data from the pressure sensor when the pump is actuated
Computing an average of the pressure data when the pump is actuated
Computing the difference between the pressure data when the pump is not actuated and the average of the pressure data when the pump is actuated Preferentially, if the value computed during the last step does not reach a predetermined value, the system performs the following steps:
Stop the pump,
Receive a pressure data from a pressure sensor when the pump is not actuated (optionally)
Actuate the pump so as to moves the fluid at a flow rate lower than the previous flow rate
Receive the pressure data from the pressure sensor when the pump is actuated
Compute an average of the new pressure data when the pump is actuated
Compute the difference between the pressure data when the pump is not actuated and the new average of the pressure data when the pump is actuated Failure Detected by a Final Test in which a Pump Generates a Greater Pressure Some tests cannot detect the failures which could have long-term impacts for the patient health. In other case, some tests minimizes the failure (in other terms, the failure seem be less important). For example, the wear of the system gradually causes a deterioration of the treatment effectiveness, and the accumulation of these less effective treatments can be hazardous for the patient. Thus, these failures have to be also detected and thus, other tests should be performed.

The detection of these failures is more complex and may be dangerous for the patient, in particular if the patient is in fluid communication with the fluidic circuit (which is tested) and/or if the test is performed before or during the treatment. Indeed, to detect these failures, the system may perform extreme tests during a longer period of time or until a partial or complete destruction of the disposable elements (tube, connector, membrane of the cassette, cassette, . . . ). For example, the aim of the new tests may be to generate a greater pressure in the dialysate circuit which can deform some element of the cassette (membrane, tube, . . . ). Thus, such test cannot be performed before or during the treatment. In other terms, these other tests may damage the cassette. Thus, these tests should be performed after the treatment, preferentially when the patient is fluidly disconnected from the system. For example if the medical treatment is a peritoneal treatment, the peritoneal cavity of the patient does not have to be in fluid communication with the dialysate circuit during these tests, thus the patient can disconnect the patient line and/or close a clamp on the patient line.

During this test, the processor may use a mathematical model so as to detect a failure, for example a mathematical model as described above.

Figure 6:
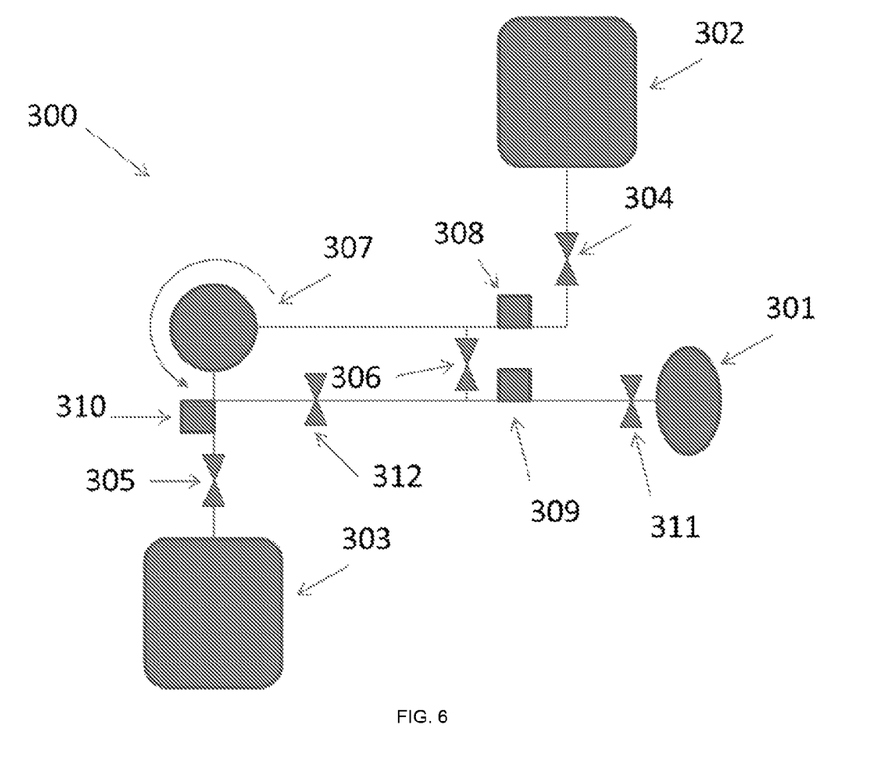
FIG. 6 illustrates an embodiment with arranged elements of the system.

For example, if this test is performed on the embodiment shown in the FIG. 6, the system (300) comprises dialysate circuit which extends between the patient (301) or the supply bag (302) and the waste fluid bag (303), a pump (307) and at least two pressure sensors (308, 309, 310). The dialysate circuit comprises a supply line, a patient line and a waste line which are respectively fluidly connected to the supply bag, the patient and the waste fluid bag. The system may comprise an occlusion element (clamp, valve, cap of connector, . . . ), said occlusion element (304, 306, 311, 305, 312) may close the supply line, the patient line and/or the waste line. Between the patient and the occlusion element (311) of the patient line, a connector (not shown) may be adapted so as to disconnect the patient form the patient line. The at least two pressure sensors may be a patient pressure sensor (309) which is in pressure communication with the patient line, a supply pressure sensor (308) which is in pressure communication with the supply line and/or a waste pressure sensor (310) which is in pressure communication with the waste line.

The sensors, the occlusion element and the pump may be electronically connected to the processor (not shown in the FIG. 6).

At the end of the treatment (for example after the medical treatment has been performed), the patient has to be disconnected from the dialysate circuit of the system (or at least no longer in fluid communication). According to the FIG. 6, if the system has two occlusion elements (306, 311), the occlusion element which is located between the pump and the patient pressure sensor has to be open while the occlusion element between the patient pressure sensor and the end of the patient line (which is adapted to be connected to the patient) has to be closed.

The occlusion element (312) may be also closed.

Optionally, the system may actuate the pump so as to check that the patient is correctly disconnected from the dialysate circuit. If the pressure sensor (309) records a drop of the pressure (for example until −80 mbar+/−80 mbar preferentially +/−40 mbar or +/−10 mbar) then the patient is correctly disconnected and/or the occlusion element (311) operates on the patient line. If the pump moves for example between 1 and 10 mL (preferentially 5 or 4 or 2 mL) without reaching −80 mbar then the patient is in fluid communication with the system.

During the test, the valves (305 and 306) are preferentially open.

During the test, the system may actuate the pump (307) so as to move the fluid from the patient line or supply line to the waste line and/or vice versa.

The test comprises the following steps:
Disconnecting the patient from the dialysate circuit,
Actuating the pump so as to generate a pressure measured by the supply pressure sensor and/or the patient pressure sensor,
Analysing by the processor the received pressure data from the supply pressure sensor and/or the patient pressure sensor.

Preferentially, the pump moves the fluid at a flowrate of 50 mL/min or 20 mL/min+/−20 mL/min preferentially +/−5 mL/min or +/−2 mL/min. To test the disconnection of the patient line, the pump may pump at 20 mL/min and to perform the final test, the pump may pump at 50 ml/min.

The pump may be adapted to generate a pressure higher than +/−200 mbar+/−10%. In this case, the pump is actuated until one sensor measures a pressure substantially equal to a predetermined threshold, for example +/−200 mbar+/−10%. Thus during the final test, the pump may be actuated until to reach −200 mbar (measured by the pressure sensors (308 and or 309). If the pump moves for example between 1 and 20 mL of fluid during the test (preferentially 15 or 10 or 5 mL) without reaching −200 mbar then the processor stops the test.

For example, the pump is actuated so as to generate a negative pressure (respectively a positive pressure) in the fluid pathway of the patient line and the supply line. The occlusion elements (304, 311 and/or 312) may be closed while the occlusion element (306) may be open. Both sensors monitor the pressure in its respective line. When one of both sensors measures a pressure which has reached a predetermine threshold (for example −250 mbar, −220 mbar, −200 mbar, −180 mbar or −150 mbar (or respectively +250 mbar, +220 mbar, +200 mbar, +180 mbar or +150 mbar)) the processor compares the measured pressure of both sensors. If the difference of measured pressure is equal to or lower than a predetermined threshold (for example +/−50 mbar or +/−40 mbar or +/−30 mbar) then the processor may conclude to a smooth operation of the system. If the difference is higher than the predetermined threshold, the system may store the data in a memory or send this data to a remote server via internet and determine that the device has potentially a problem.

The system may store several data of this difference and it may use this data to monitor a trend, for example the number of times that the threshold is reached or the proportion of the threshold reached. If one or all conditions is reached, then the system may indicate to the patient (via a screen of the system or other indication device) that the system requires maintenance (now or in few days or before a number of treatments) and/or may send this information to a remote service center via e.g. internet.

Preferentially, the pump is actuated during a predetermined time or until reaching a predetermined number of pump strokes or a predetermined pressure or when a predetermined volume has been moves by the pump (for example 10 ml, 5 ml or 4 ml preferentially +/−2 ml or +/−1 ml).

For all tests, the device may record the data of the test and/or a report of the test and/or alerts the patient. Said data or report may be monitored by the processor in such a manner as to predict a potential future failure of an element or to predict the overhaul date of the device (as the expected date of revision). All or part of these data may be sent to a remote server.

Such final test (done after completion of the treatment and while the patient is disconnected from the device) can be extremely useful to confirm the normal operation of the device and/or detection of specific malfunctions, without requiring a specific servicing nor extra cost or time (the set used for such test is the same as the one used for the treatment which is, at such time, to be discarded).

The invention claimed is:

1. A method for detecting a failure in a system for providing a medical treatment to a patient, the system including a fluid pathway in removable fluidic communication with the patient, a pump, an occlusion element for the fluid pathway, and a sensor for measuring a pressure in the fluid pathway, the pump and the sensor operatively connected to an electronic processor, the pump configured to move a fluid through the fluid pathway, the system configured to infuse or remove the fluid to or from the patient via the fluid pathway, the method comprising the steps of:
- blocking the fluidic communication between the patient and the fluid pathway after the medical treatment is completed;
- performing a test to detect an operational failure of the system, the performing the test including,
    - actuating the pump,
    - measuring a pressure by the sensor in the fluid pathway,
    - monitoring the measured pressure by the electronic processor,
    - determining by the electronic processor whether the operational failure is present based on the monitored pressure,
    - stopping the pump when at least one of the monitored pressure reaches a predetermined threshold, a number of pump stroke reaches a predetermined value, and a duration of the test reaches a predetermined time value; and
    - determining the operational failure of the system when the pump is stopped before the measured pressure has reached the predetermined threshold.

2. The method as in claim 1, wherein the system includes a reusable part and a disposable and non-reusable part, wherein the step of performing the test renders unusable the disposable and non-reusable part.

3. The method as in claim 1, further comprising the step of:
- disconnecting the fluid pathway from the patient before the step of performing the test.

4. The method as in claim 1, further comprising the step of:
- checking that the patient is no longer in fluidic communication with the fluid pathway before the step of performing the test.

5. The method as in claim 1, further comprising the step of:
- preventing the step of performing the test when the patient is fluidly connected to the fluid pathway.

6. The method as in claim 1, wherein the occlusion element includes at least one of a valve, connection cap, and clamp configured to close at least a part of the fluid pathway.

7. The method as in claim 6, wherein the step of blocking the fluid pathway further includes,
- closing the fluid pathway via the occlusion element to define a closed pathway between the pump and the occlusion element, and
- wherein the step of actuating the pump generates the pressure in the closed fluid pathway.

8. The method as in claim 1, further comprising the step of:
- at least one of recording data in a memory of the system, sending the data to a remote server, and alerting the patient of the operational failure of the system, upon detecting the failure by the step of performing the test.

9. The method as in claim 1, wherein the operational failure of the system includes a leakage of the fluid pathway caused by a decoupling of the sensor to the fluidic pathway.

10. The method as in claim 1, wherein the operational failure of the system includes an improper interconnection of a cassette for holding the fluid to the fluid pathway.

11. The method as in claim 1, wherein the operational failure of the system includes a wear of the system.

* * * * *